United States Patent [19]
Arnold et al.

[11] Patent Number: 5,919,964
[45] Date of Patent: *Jul. 6, 1999

[54] METHOD FOR THE PREPARATION OF PURE CARBOXYETHYL GERMANIUM SESQUIOXIDE

[75] Inventors: Michael J. Arnold, Irvine; Daniel Horne, Mountain View, both of Calif.

[73] Assignee: Viva America Marketing, Inc., Costa Mesa, Calif.

[ * ] Notice: This patent is subject to a terminal disclaimer.

[21] Appl. No.: 08/977,516

[22] Filed: Nov. 24, 1997

Related U.S. Application Data

[63] Continuation-in-part of application No. 08/577,307, Dec. 22, 1995, Pat. No. 5,703,259, which is a continuation-in-part of application No. 08/381,343, Jan. 31, 1995, Pat. No. 5,550,266, which is a continuation-in-part of application No. 08/204,548, Mar. 2, 1994, Pat. No. 5,386,046.

[51] Int. Cl.$^6$ ........................................................ C07F 7/30
[52] U.S. Cl. ................................ 556/89; 556/89; 556/105
[58] Field of Search ................................ 556/87, 89, 105

[56] References Cited

U.S. PATENT DOCUMENTS

| | | | |
|---|---|---|---|
| 3,793,455 | 2/1974 | Asai et al. | 424/287 |
| 4,066,678 | 1/1978 | Sato et al. | 260/429 |
| 4,473,581 | 9/1984 | Ishida et al. | 424/287 |
| 4,898,882 | 2/1990 | Nagahama et al. | 514/492 |
| 4,956,272 | 9/1990 | Kakimoto et al. | 435/1 |
| 4,973,553 | 11/1990 | Miyano et al. | 435/206 |
| 4,977,287 | 12/1990 | Kakimoto et al. | 556/83 |
| 5,386,046 | 1/1995 | Arnold | 556/89 |
| 5,550,266 | 8/1996 | Arnold | 556/89 |
| 5,703,259 | 12/1997 | Arnold | 556/89 |

FOREIGN PATENT DOCUMENTS

| | | |
|---|---|---|
| 3345211 A1 | 6/1985 | Germany . |
| 53-127882 | 11/1978 | Japan . |
| 53-130483 | 11/1978 | Japan . |
| 54-160319 | 12/1979 | Japan . |
| 56-128789 | 10/1981 | Japan . |
| 57-67588 | 4/1982 | Japan . |
| 61-148186 | 7/1986 | Japan . |
| 2 190 835 | 12/1987 | United Kingdom . |
| 2 222 404 | 3/1990 | United Kingdom . |

*Primary Examiner*—Porfirio Nazario-Gonzalez
*Attorney, Agent, or Firm*—Covington & Burling

[57] ABSTRACT

This invention provides a method for synthesizing pure carboxyethyl germanium sesquioxide that does not include any toxic impurities, such as germanium dioxide or metallic germanium. Neither of these toxic compounds is used as a starting material. The method involves steps which ensure the full reaction of germanium tetrachloride in order to ensure that none is available to form germanium dioxide and steps which ensure the removal of any germanium dioxide.

8 Claims, No Drawings

METHOD FOR THE PREPARATION OF PURE CARBOXYETHYL GERMANIUM SESQUIOXIDE

RELATED APPLICATIONS

This application is a continuation-in-part of U.S. patent application Ser. No. 08/577,307, filed Dec. 22, 1995, now U.S. Pat. No. 5,703,259 which is a continuation-in-part of U.S. patent application Ser. No. 08/381,343, filed Jan. 31, 1995, now U.S. Pat. No. 5,550,266, issued Aug. 27, 1996, which is a continuation-in-part of U.S. patent application Ser. No. 08/204,548, filed Mar. 2, 1994, U.S. Pat. No. 5,386,046, issued Jan. 31, 1995.

BACKGROUND

1. Field of the Invention

The present invention relates to a method for synthesizing pure carboxyethyl germanium sesquioxide, and in particular to a chemical method for synthesizing, in bulk quantities, carboxyethyl germanium sesquioxide without trace amounts of germanium dioxide or metallic germanium.

2. Background of the Invention

It is understood that certain forms of germanium confer various health benefits to humans. [See, e.g., U.S. Pat. No. 4,595,882; U.S. Pat. No. 3,793,455]. Although synthetic carboxyethyl germanium sesquioxide is a well known compound, its molecular structure has been shown to be dependent on the synthetic method employed. Uses of germanium in the human diet include preventing the overproliferation of cells, stimulating the production of interferon, and inducing contrasuppressor T cells. [See, e.g., F. Suzuki and R. Pollard, *J. Interferon Res.*, 4(2) :223–33 (1984); P. Kopf-Maier, *Eur. J. Clin. Pharmacol.*, 47:1–16 (1994); K. Ikemoto et al., *Expermentia*, 52:159–166 (1996)].

In order to use germanium as a dietary supplement, the carboxyethyl germanium sesquioxide needs to be pure, that is, essentially free of unwanted and potentially toxic contaminants germanium dioxide and metallic germanium. Many known methods for synthesizing carboxyethyl germanium sesquioxide provide for the production of germanium sesquioxide contaminated with trace amounts of metallic germanium or germanium dioxide, since these are used as the starting materials.

The key intermediates common to such known synthetic routes are trichlorogermanium acrylate moieties (trichlorogermanium acryl chlorides, trichlorogermanium acrylic acids, trichlorogermanium acroleins and trichlorogermanium alkyl acrylates), and known methods of synthesizing trichlorogermanium acrylate intermediates require either oxidation of metallic germanium with hydrochloric acid, or reduction of germanium dioxide. The problem with such methods is the significant probability of generating trace amounts of unreacted starting material (metallic germanium or germanium dioxide) in the product.

Background Art

As stated above, it is known that certain forms of germanium may be used to confer certain health benefits to humans [See, e.g., U.S. Pat. No. 4,595,882; U.S. Pat. No. 3,793,455, F. Suzuki and R. Pollard (cited above), P. Kopf-Maier (cited above), and K. Ikemoto et al. (cited above)].

Although the synthesis of germanium compounds of various structures has been reported, in these instances, the synthesis is typically accomplished with metallic germanium or germanium dioxide, resulting on the potential for residual toxic starting materials in the final products. The present invention does not start with either metallic germanium or germanium dioxide, but rather starts with germanium tetrachloride.

SUMMARY OF THE INVENTION

An object of the present invention to provide a method of synthesizing carboxyethyl germanium sesquioxide that is devoid of the aforementioned drawbacks which to date have characterized this art—most particularly the possibility for residual toxic starting materials in the final product dietary supplement compositions.

It is another object of the present invention to provide a method whereby carboxyethyl germanium sesquioxide can be prepared without contamination from metallic germanium or germanium dioxide.

It is yet a further object of the present invention to provide a method for the production of a carboxyethyl germanium sesquioxide molecular species that is substantially non-toxic to the human body.

It is yet another object of the present invention to provide a method of producing carboxyethyl germanium sesquioxide molecular species that has an LD50 value of at least 5 g/kg.

It is yet a further object of the present invention to provide a method of synthesizing carboxyethyl germanium sesquioxide comprising the steps of:

(1) reacting germanium tetrachloride and tetramethyldisiloxane and acrylic acid to form a first reaction mixture of trichlorogermanium propionic acid (TPA), a germanium acrylate reaction product, and volatile by- products;

(2) distilling the first reaction mixture to remove the volatile by-products thereby forming a second reaction mixture of TPA and germanium acrylate reaction product;

(3) reacting the second reaction mixture with HCl to form a third reaction mixture of TPA and HCl;

(4) extracting with a halogenated solvent the HCl from the third reaction mixture to form a fourth reaction mixture of halogenated solvent and TPA;

(5) vacuum distilling the fourth reaction mixture to remove the halogenated solvent thereby forming a fifth reaction mixture of crude TPA crystals;

(6) dissolving the crude TPA crystals in a heated non-polar alkyl solvent to form a sixth reaction mixture;

(7) cooling the sixth reaction mixture to form TPA crystals;

(8) filtering and washing the TPA crystals in a heated non-polar alkyl solvent to form pure TPA crystals;

(9) reacting the pure TPA crystals in water to form carboxyethyl germanium sesquioxide; and

(10) isolating the carboxyethyl germanium sesquioxide.

These and other objects of the present invention will be further described in the detailed description section that follows.

DETAILED DESCRIPTION OF THE INVENTION

The method of the present invention involves the isolation and purification of the intermediate trichlorogermanium propionic acid (TPA). In this method, the reaction of germanium tetrachloride in the presence of acrylic acid takes place under ambient conditions to form a germanium acrylate reaction product and TPA. To this mixture is then added concentrated hydrochloric acid to form a crude TPA reaction product, which is then recrystallized to form a substantially pure TPA. The pure TPA is then hydrolyzed to form substantially pure carboxyethyl germanium sesquioxide.

The method of the invention involves the steps of forming the intermediate trichlorogermanium propionic acid (TPA) from the starting material of germanium tetrachloride, isolating and purifying the TPA, and converting the TPA by hydrolysis to carboxyethyl germanium sesquioxide.

The specific steps of the process are described in the following general protocol—variations of this protocol are further detailed below and are within the scope of the present invention. The steps of the general protocol are as follows:

(1) reacting germanium tetrachloride and tetramethyldisiloxane and acrylic acid to form a first reaction mixture of TPA, a germanium acrylate reaction product, and volatile by-products;

(2) distilling the first reaction mixture to remove the volatile by-products thereby forming a second reaction mixture of TPA and a germanium acrylate reaction product;

(3) reacting the second reaction mixture with HCl to form a third reaction mixture of TPA and HCl;

(4) extracting with a halogenated solvent the HCl from the third reaction mixture to form a fourth reaction mixture of halogenated solvent and TPA;

(5) vacuum distilling the fourth reaction mixture to remove the halogenated solvent thereby forming a fifth reaction mixture of crude TPA crystals;

(6) dissolving the crude TPA crystals in a heated non-polar alkyl solvent to form a sixth reaction mixture;

(7) cooling the sixth reaction mixture to form TPA crystals;

(8) filtering and washing the TPA crystals in a heated non-polar alkyl solvent to form pure TPA crystals;

(9) reacting the pure TPA crystals in water to form carboxyethyl germanium sesquioxide; and

(10) isolating the carboxyethyl germanium sesquioxide.

Step 1

More specifically, in a preferred embodiment, the first step involves reacting germanium tetrachloride with tetramethyldisiloxane and acrylic acid to form a first reaction mixture consisting substantially of trichlorogermanium propionic acid (TPA), a germanium acrylate reaction product, and volatile by-products. The preferred time for the reaction of the first step is from about 30 to about 45 days. The preferred internal temperature for the first reaction step is from about 20° C. to about 25° C., and the preferred pressure is about 1 atm. Although other amounts may be used, in a preferred embodiment, 1 mole of germanium tetrachloride is reacted with 1 mole of tetramethyldisiloxane and 1.7 moles acrylic acid. The reaction profile is:

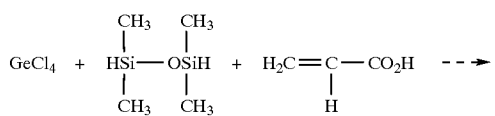

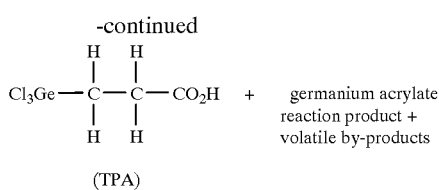

(TPA)

Step 2

As a second step in a preferred embodiment, the first mixture is subjected to vacuum distillation to remove the volatile by-products. The preferred vacuum is from about 0.1 Torr to about 25 Torr, most preferably from about 0.25 Torr to about 15 Torr, and most preferably from about 0.5 Torr to about 5 Torr. The internal temperature for this vacuum distillation is from about 60° C. to about 75° C. This distillation results in a second reaction mixture which consists substantially of TPA plus the germanium acrylate reaction product. The reaction profile of this step is:

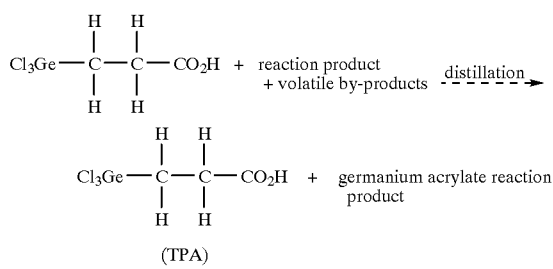

Step 3

In a preferred embodiment, the second reaction mixture is next reacted with HCl in an amount at least sufficient to react with the germanium acrylate reaction product in such fashion that the germanium reaction product is converted to TPA. Therefore, this step results in a mixture of TPA and HCl. The preferred amount of HCl is from about 0.25 to about 10 mass equivalents (compared to the mass of germanium tetrachloride), and the most preferred from about 0.5 to about 3 mass equivalents. The preferred temperature of the reaction is from about 60° C. to about 85° C., and the preferred time of the reaction is from about 30 minutes to about 4 hours, and the most preferred is from about 45 minutes to about 90 minutes. The result is a third mixture consisting substantially of a heterogeneous mixture of white solid TPA and aqueous concentrated HCl. The reaction profile of this step is:

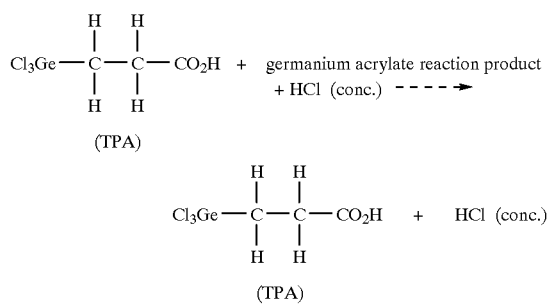

Step 4

In the next step in a preferred embodiment, the third mixture is subjected to solvent extraction to separate the hydrochloric acid from the TPA, thus yielding a fourth mixture that consists substantially of TPA and the extraction solvent. Suitable extraction solvents, in an amount sufficient to extract all of the HCl, include halogenated solvents such as chloroform and carbotetrachloride, and preferably, dichloromethane. The amount of halogenated solvent used in the extraction is from about 1 to about 30 mass equivalents (to the starting mass of germanium tetrachloride), and most preferably from about 3 to about 8 mass equivalents. Preferably an excess amount of extraction solvent is used to ensure that no HCl remains in the fourth mixture. An exemplary reaction profile (using dichloromethane, $H_2CCl_2$) for this step is:

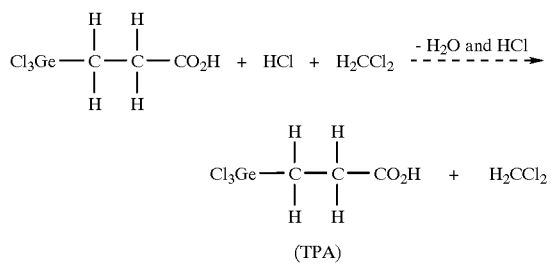

(TPA)

Step 5

In a preferred embodiment, the next step comprises vacuum distilling the fourth mixture to remove the extraction solvent (e.g., $H_2CCl_2$ in the exemplary formula depicted above) resulting in a fifth reaction mixture of crude TPA reaction product, consisting substantially, but not purely, of TPA crystals. The preferred vacuum is from about 0.1 Torr to about 25 Torr, more preferably from about 0.25 Torr to about 15 Torr, and most preferably from about 0.5 Torr to about 5 Torr. The preferred internal temperature for this vacuum distillation is from about 10° C. to about 35° C. An exemplary reaction profile for this step is:

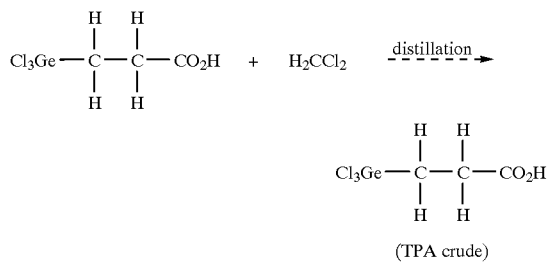

(TPA crude)

Steps 6 and 7

The next steps of a preferred embodiment of the process of the present invention convert the crude TPA crystals into pure TPA, and then further into carboxyethyl germanium sesquioxide. This is accomplished by next bringing the crude TPA reaction product into solution via reflux using the stepwise addition of a minimal amount of non-polar alkyl solvent, including but not limited to solvents such as hexane, heptane, and pentane. After a homogeneous solution is obtained, the addition of the solvent is ceased, and this sixth mixture is slowly cooled to ambient temperature. This sixth mixture is allowed to stand at room temperature for at least about 12 hours, and most preferably about 24 hours, at the end of which period TPA crystals have formed. These TPA crystals remain in solution of the solvent.

Step 8

In a preferred embodiment, the next step comprises filtering the solution with TPA crystals solution using a paper filter or suction filtration using buchner-type filters. The resulting TPA crystals are then washed successively with a non-polar alkyl solvent, such as hexane, in order to yield crystals of pure TPA of the formula $Cl_3GeC_2H_4CO_2H$. The preferred temperature for this filtrating and washing step is ambient temperature, and the preferred amount of solvent that may be used is 1 mass equivalent of solvent to TPA crystals.

Steps 9 and 10

In the final steps in a preferred embodiment, the pure TPA crystals are then reacted under reflux conditions with the stepwise addition of a minimal amount of distilled water. By a minimal amount it is meant that only enough distilled water is added to cause the crystals to dissolve into solution. A preferred amount of distilled water is from about 15 to about 25 mass equivalents (compared to the mass of TPA). The preferred internal temperature is from about 75° C. to about 100° C. The reflux time is preferably from about 1 to about 3 hours. After the crystals are dissolved, the addition of distilled water is ceased, and the solution is allowed to cool to ambient temperature and allowed to stand for at least about 12 hours, and most preferably from about 24 hours to about 48 hours. The result is pure, solid germanium sesquioxide which is then filtered, using a gravity filter and filter paper (such as Watman #4 paper) or using suction filtration (buchner-type) using filter paper (such as Watman #2 paper). The filtered solution is then washed successively with water, acetone, and finally ether. The water wash is from about 1 mass equivalent (compared to TPA) to about 10 mass equivalents, most preferably from about 2 to about 4 mass equivalents. The acetone wash is from about 1 to about 10 mass equivalents (compared to TPA), and preferably from about 2 to about 4 mass equivalents. Finally, the ether wash is from about 1 to about 10 mass equivalents (compared to TPA), and preferably from about 2 to about 4 mass equivalents. The chemical formula of pure carboxyethyl germanium sesquioxide is $Ge_2C_6H_{10}O_7$ The purified and isolated carboxyethyl germanium sesquioxide may then be used, for example, in dietary supplements to confer the health benefits described above. One of the benefits to method of producing carboxyethyl germanium sesquioxide of the present invention is that it provides a safe and efficacious form of germanium for use by the human body.

In particular, the present invention eliminates the possibility that metallic germanium can find its way into a dietary supplement since the starting materials and methods do not have the potential for producing any metallic germanium. In addition, the present invention eliminates the potential for germanium dioxide to wind up in the dietary supplements that incorporate the carboxyethyl germanium sesquioxide produced by the method of the present invention. This is for two principal reasons. First, the recrystallization step of the above-described process eliminates any germanium dioxide that may have resulted from any of the prior steps. Second, the method the present invention works to eliminate any germanium dioxide even before the recrystallization step. Specifically, any germanium dioxide present in the method of the present invention would be present only as a by-product of the germanium tetrachloride used in the first reaction step. In other words, in the initial reaction of germanium tetrachloride with tetramethyldisiloxane and acrylic acid, it is theoretically possible that there remains unreacted germanium tetrachloride which could potentially hydrolyze to form germanium dioxide. However, the second step of vacuum distillation would remove any remaining unreacted germanium tetrachloride, thereby preventing the formation of additional germanium dioxide through hydrolysis. Even if any germanium dioxide remains as a by-product in the aqueous phase, such germanium dioxide is removed and discarded via the subsequent extraction and distillation steps of the process. For example, the next step in the process (i.e., the third step in the preferred embodiment described above), reaction with hydrochloric acid would convert any germanium dioxide by-product to germanium tetrachloride. If any germanium dioxide remained after the distillation and extraction steps, it would be observed as a solid during the next step of solvent extraction with a halogenated solvent because germanium dioxide is insoluble in halogenated solvents. Since no germanium dioxide is observed, it is clear that no germanium dioxide is present in the organic phase. Moreover, the next step of vacuum distillation would remove any remaining germanium tetrachloride produced from the reaction of HCl and germanium dioxide, thereby eliminating the possibility that any germanium tetrachloride or germanium dioxide remain in the reaction mixture. As a result, the method of the present invention provides a resulting carboxyethyl germanium sesquioxide product of sufficient purity for human consumption.

The method of carboxyethyl germanium sesquioxide production of the present invention has additional advantages. For example, the present method provides a pure carboxyethyl germanium sesquioxide in high yield. By high yield, it is meant that there is an increase of about 10% to about 20% in yield of pure carboxyethyl germanium sesquioxide over conventional methods for producing carboxyethyl germanium sesquioxide. It is possible, moreover, that the present invention can result in yield increases even higher than 20% over conventional methods. Another advantage to the present method is that it avoids the use of caustic, toxic and dangerous chemicals (such as ammonium hydroxide and sulfuric acid) used in conventional methods for synthesizing germanium. In addition, the present process uses a substantially reduced amount of HCl over previously known methods, such as those described in U.S. Pat. Nos. 5,504,225 and 5,386,046. As a result, the process of the present invention has ecological benefits, and can save a substantial amount of time, labor, and resources in the manufacturing process.

The use carboxyethyl germanium sesquioxide is also understood to have beneficial health effects for humans. For daily health maintenance, a dosage range of from about 10 mg/day to about 200 mg/day is advised. In order to address pre-existing health conditions, for example influenza symptoms, a daily solid dosage form ranges from about 10 mg/day to about 10,000 mg/day. For an injectable solution used to treat pre-existing conditions, the amount of germanium sesquioxide dose is from about 10 mg/day to about 1,000 mg/day, and preferably from about 30 mg/day to about 300 mg/day.

The carboxyethyl germanium sesquioxide compositions of the present invention are stable compounds and may be combined with other dietary supplement ingredients. These preparations may be made by conventional methods. To prepare the compositions of the invention, the ingredients are combined in one preparation as the active ingredient in intimate admixture with a suitable carrier or excipients according to conventional compounding techniques. The compositions of the present invention are compatible with commonly used excipients such as maltodextrin and microcrystalline cellulose.

Suitable carriers may take a wide variety of forms depending upon the form of preparation desired for administration, e.g., oral, sublingual, nasal, or parenteral.

In preparing the compositions in oral dosage form, any of the usual pharmaceutical media may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, gelatin capsules, pills, and tablets). Gelatin capsules are a preferred oral dosage form. Lozenges, microencapsulated tablets, and other controlled release forms may also be used. Because of their ease in administration, lozenges, tablets, pills, and capsules represent the most advantageous oral dosage unit form, in which case solid pharmaceutical carriers are obviously employed. If desired, tablets may be sugar coated, enteric coated or microencapsulated by standard techniques.

For parenteral products, the carrier will usually comprise sterile water, although other ingredients may be included, e.g., to aid solubility or for preservation purposes. Injectable suspensions may also be prepared, in which case appropriate liquid carriers, suspending agents, and the like may be employed.

As an alternative embodiment to the method described above, one may vary the steps in that:

(1) the reaction time of the first step can be increased from about 7 days to from between about 30 days to about 120 days, and preferably about 45 days;

(2) the amount of concentrated hydrochloric acid used in the third step can be reduced;

(3) the reaction time of the fourth step, i.e., the step yielding TPA, can be reduced;

(4) the ninth step (converting pure TPA into pure germanium sesquioxide) is changed by substituting either of ammonia or sulfuric acid for water; and (5) the pure TPA crystals are dissolved and reacted for a sufficient period of time in hot water for a period of time long enough to dissolve the crystals, then cooled to directly form carboxyethyl germanium sesquioxide.

The following examples demonstrate several preferred embodiments of the present invention, and are therefore non-limiting.

EXAMPLE 1

A specific example of the process described above is as follows. To a 50 L glass reactor is added successively 7.2 kg germanium tetrachloride, 5.3 kg tetramethyl disiloxane, and 2.32 kg of acrylic acid. The resulting mixture is stirred for 45 days forming TPA (trichlorogermanium propionic acid) as a product. Volatile by-products are removed via vacuum distillation while the TPA product is heated to an internal temperature of 650° C. to 800° C., where it is a homogeneous, colorless, viscous solution. Distillation is continued until no more distillate appears, leaving a semi-viscous (molten) crude TPA product. To the molten product is then added 4.8 L of concentrated HCl. The resulting heterogeneous mixture is warmed to an internal temperature of 60° C.–70°C., and stirred for 30 minutes and allowed to cool.

The cooled mixture is extracted 3 times with 25 L of dichloromethane. The dichloromethane is removed via vacuum distillation to yield an amorphous white solid of TPA. This TPA solid is dissolved in 38 L of hexane, then cooled to ambient temperature, where fine TPA crystals are formed within 24 hours.

The solid is filtered and then resuspended in 30 mL of distilled water, and then heated to reflux until the mixture becomes homogeneous. The solution is then refluxed for 4 hours, and then cooled to ambient temperature, whereby crystals of carboxyethyl germanium sesquioxide form over a period of about 48 hours. The white carboxyethyl germanium sesquioxide solid is isolated via suction filtration, washed successively with 2×5.4 L acetone, and 2×5.4 L of diethyl ether. The resulting brilliant white carboxyethyl germanium sesquioxide solid is dried overnight in a vacuum oven at 40° C.

EXAMPLE 2

To a 50 L glass reactor is added successively: 72 g of germanium tetrachloride, 5.3 kg of tetramethyldisiloxane, and 2.32 kg of acrylic acid, and the resulting reaction mixture is stirred for 5 days. Volatile by-products are removed via vacuum distillation while the product mixture is heated to an internal temperature of 75° C. to 80° C., where it is a homogenous, colorless, semi-viscous solution (molten) . Distillation is continued until no more distillate appears. This reaction mixture is cooled to ambient temperature yielding a white amorphous solid.

This solid is then dissolved in 35 L of concentrated HCl. The resulting heterogeneous mixture is warmed to an internal temperature of 60° C.–70° C., and stirred for four hours. The cooled mixture is extracted 3 times with 25 L of dichloromethane. The dichloromethane is removed with vacuum distillation at 40° C. to give a white amorphous solid of crude TPA.

This TPA solid is immediately taken up (vigorous action) with careful addition of 30 L of ammonium hydroxide (29% ammonia). The resulting mixture is stirred for 4 days at ambient temperature. To this, 400 mL of concentrated sulfuric acid is added dropwise over two hours through a reflux condenser. The white TPA solid is isolated via suction filtration, washed successively with 2×5.4 L water, 2×5.4 L acetone, and 2×5.4 L of diethyl ether, then this brilliant white, pure TPA solid is air dried overnight. This pure TPA solid is then taken up with 9 L of hot distilled water, then cooled and filtered to yield carboxyethyl germanium sesquioxide.

EXAMPLE 3

An exemplary mixture of a food supplement using organic carboxyethyl germanium sesquioxide is:

| Pangamic acid | 50 | mg |
| carboxyethyl germanium sesquioxide* | 25 | mg |
| Co-Enzyme Q10 | 25 | mg |
| Vitamin A | 1,250 | I.U. |
| Vitamin E | 100 | I.U. |
| Vitamin D | 7.5 | I.U. |
| Vitamin K | 125 | mg |

*carboxyethyl germanium sesquioxide may be prepared by any of the methods of the present invention described above Although particular embodiments of the invention have been described and illustrated herein, it is recognized that modifications and variations readily occur to those skilled in the art, and consequently it is intended that the claims be interpreted to cover such modifications and equivalents.

We claim:

1. A method of preparing substantially pure carboxyethyl germanium sesquioxide comprising the steps of:

reacting germanium tetrachloride, tetramethyldisiloxane, and acrylic acid to form a first reaction mixture of TPA, a germanium acrylate reaction product, and volatile by-products;

distilling the first reaction mixture to remove the volatile by-products, thereby forming a second reaction mixture of TPA and germanium acrylate reaction product;

reacting the second reaction mixture with HCl to form a third reaction mixture of TPA and HCl;

extracting with a halogenated solvent the HCl from the third reaction mixture to form a fourth reaction mixture of halogenated solvent and TPA;

vacuum distilling the fourth reaction mixture to remove the halogenated solvent thereby forming a fifth reaction mixture of crude TPA crystals;

dissolving the crude TPA crystals in a heated non-polar alkyl solvent to form a sixth reaction mixture;

cooling the sixth reaction mixture to form TPA crystals;

filtering and washing the TPA crystals in a heated non-polar alkyl solvent to form pure TPA crystals;

reacting the pure TPA crystals in water to form carboxyethyl germanium sesquioxide; and isolating the carboxyethyl germanium sesquioxide.

2. The method of claim 1 wherein the first distilling step of trichlorogermanium propionic acid is vacuum distilling.

3. The method of claim 1 wherein the first reacting step further comprises reacting an amount of tetramethyldisiloxane and acrylic acid reactants with the germanium tetrachloride sufficient to ensure full reaction of the germanium tetrachloride.

4. The method of claim 1 wherein the volatile by-products of the first reacting step include unreacted germanium tetrachloride, and when the first reacting step further comprises removing the volatile by-products by vacuum distillation.

5. The method of claim 1 wherein the second reacting step further comprises adding an amount of hydrochloric acid sufficient to ensure reaction of any germanium dioxide to germanium tetrachloride.

6. The method of claim 1 wherein the extraction solvent in the extracting step comprises dichloromethane.

7. The method of claim 1 further comprising the step of observing the fourth reaction mixture for any solid germanium dioxide, and removing any such germanium dioxide present.

8. The method of claim 1 wherein extracting step removes any residual germanium tetrachloride.

\* \* \* \* \*